United States Patent
Ukigaya et al.

[11] Patent Number: 6,106,863
[45] Date of Patent: Aug. 22, 2000

[54] SUSTAINED-RELEASE METAL VALPROATE TABLETS

[75] Inventors: Tadashi Ukigaya; Mutsuo Okumura; Tadashi Tsukune, all of Saitama, Japan

[73] Assignee: Nikken Chemicals Co., Ltd., Tokyo, Japan

[21] Appl. No.: 09/142,561

[22] PCT Filed: Mar. 12, 1997

[86] PCT No.: PCT/JP97/00780

§ 371 Date: Sep. 11, 1998

§ 102(e) Date: Sep. 11, 1998

[87] PCT Pub. No.: WO97/33574

PCT Pub. Date: Sep. 18, 1997

[30] Foreign Application Priority Data

Mar. 15, 1996 [JP] Japan .................. 8-086052
Feb. 18, 1997 [JP] Japan .................. 9-048577

[51] Int. Cl.[7] .............. A61K 9/22; A61K 9/32; A61K 9/36
[52] U.S. Cl. ............ 424/480; 424/468; 424/474; 424/475; 424/482; 514/770; 514/781; 514/772.3
[58] Field of Search ............ 424/474, 475, 424/480, 482, 495, 497, 468

[56] References Cited

U.S. PATENT DOCUMENTS

| | | | |
|---|---|---|---|
| 4,913,906 | 4/1990 | Friedman et al. | 424/499 |
| 5,019,398 | 5/1991 | Daste | 424/480 |
| 5,169,642 | 12/1992 | Brinker et al. | 424/488 |

FOREIGN PATENT DOCUMENTS

| | | | |
|---|---|---|---|
| 60-41610 | 3/1985 | Japan | A61K 31/19 |
| 62-081309 | 4/1987 | Japan . | |
| 62-084020 | 4/1987 | Japan . | |
| 1-290628 | 11/1989 | Japan | A61K 31/415 |
| 2-218621 | 11/1990 | Japan . | |
| 3-190817 | 8/1991 | Japan | A61K 9/62 |
| 4-235914 | 8/1992 | Japan | A61K 31/20 |
| 6-40899 | 2/1994 | Japan | A61K 31/19 |
| 8-26977 | 1/1996 | Japan | A61K 9/50 |

*Primary Examiner*—James M. Spear
*Attorney, Agent, or Firm*—Sughrue, Mion, Zinn, Macpeak & Seas, PLLC

[57] ABSTRACT

The present invention provides a sustained-release metal valproate tablet which is comparatively compact and is not influenced by a meal, the sustained-release metal valproate comprising a core tablet comprising a metal valproate having on the surface a coating layer comprising light silicic acid anhydride dispersed in a mixture of ethyl cellulose and a methacrylic acid-methyl methacrylate copolymer.

9 Claims, 2 Drawing Sheets

DISSOLUTION TEST RESULTS
(THE PHARMACOPOEIA OF JAPAN, 2ND SOLUTION 900ml)

DISSOLUTION TEST RESULTS
(THE PHARMACOPOEIA OF JAPAN, 2ND SOLUTION 900ml)

CHANGES OF VALPROIC ACID CONCENTRATION
MEASN±S.D. (n = 6)

SUSTAINED-RELEASE METAL VALPROATE TABLETS

This application is a 371 of PCT/JP97/00780 filed Mar. 12, 1997.

TECHNICAL FIELD

The present invention relates to sustained-release metal valproate tablets.

BACKGROUND

Sodium valproate is a useful drug widely used for the treatment of epilepsy and prevention of *ictus epilepticus*. The effective blood concentration of the drug is generally in the range of 50 to 100 µg/ml. Since sodium valproate has a short biological half-life, it should be administered three times a day to keep the effective blood concentration. Such a short does interval being troublesome for patients, many efforts have been made to develop sustained-release preparations of sodium valproate, and several preparations have now been on the market. However, sodium valproate should be administered at a comparatively high daily dose reaching 1200 mg. Besides, it is water-soluble and highly hygroscopic. Hence, sustained-release tablets prepared by conventional techniques comprise a comparatively large proportion of release retarders, and the like, which increase the weight of the individual tablets, and are not always satisfactory.

Some proposals have been made on sustained-release tablets of sodium valproate.

For example, known are a method of preparing granules from a mixture of sodium valproate and magnesium aluminometasilicate using ethyl cellulose as a binder and then preparing sustained-releasing tablets (JP-A-62-81309) and a method of adding valproic acid in which ethyl cellulose has been dissolved therein to a mixture of Eudragit (a methacrylic acid copolymer) and sodium valproate, granulating the mixture, and preparing tablets (JP-A-60-41610). However, it is difficult to keep the blood concentration of sodium valproate for a long time according to these techniques.

JP-A-8-26977 discloses controlled-release oral preparations, which are applicable to general drugs, comprising a drug-containing core coated with a dissolution controlling coat comprising a mixture of a water-insoluble film-forming agent and an enteric film-forming agent. JP-A-8-26977 discloses a controlled-release oral preparation prepared by using a mixture of ethyl cellulose as a water-insoluble film-forming agent and a methacrylic acid-methyl methacrylate copolymer as an enteric film-forming agent. Judging from the specification as a whole, however, this invention relates to granules or powders the coat of which does not dissolve to release the drug in the stomach and the upper part of the small intestine but quickly dissolves to release the drug in the lower part of the digestive tract having a comparatively high pH, i.e., the lower part of the small intestine and the large intestine. Therefore, it is different from the present invention in not only purpose but also a preferred mixing ratio of ethyl cellulose and a methacrylic acid-methyl methacrylate copolymer.

Moreover, JP-A-4-235914 discloses a method of coating a core tablet containing sodium valproate with a coating agent comprising ethyl cellulose and hydroxypropylmethyl cellulose that is a water-soluble polymer.

The inventors of the present invention previously invented a sustained-release sodium valproate tablet which comprises a core tablet comprising sodium valproate having on the surface a coating layer coated with a coating agent comprising light silicic acid anhydride dispersed in ethyl cellulose (JP-A-6-40899). The sustained-release tablet exhibits satisfactory sustained release properties, showing substantially no difference in dissolution rate with pH change in a dissolution test using first and second solutions specified in The Pharmacopoeia of Japan. However, cases are sometimes observed with the sustained-release tablet having a release-controlling coating layer, wherein valproic acid is released from sodium valproate by the action of an acidic liquid having passed through the sustained-release coating layer in the digestive tract (stomach), and the valproic acid thus released dissolves and erodes the coating layer. If the tablet is taken during active peristalsis after a meal, it may follow that the coating layer is destroyed by the influences of the meal to accelerate dissolution of sodium valproate. In this case the sustained-release tablet fails to keep a preferred blood concentration.

The inventors have extensively continued their study on sustained-release tablets which can be administered once a day and are free from the influences of a meal, and found that a coating layer comprising ethyl cellulose and a methacrylic acid copolymer does not dissolve in valproic acid. As a result of further study based on this finding, they have reached the finding that a tablet obtained by coating a core comprising sodium valproate with a coating agent comprising light silicic acid anhydride uniformly dispersed in ethyl cellulose and a methacrylic acid copolymer is comparatively compact and exhibits extremely stable and satisfactory sustained release properties even in an acidic liquid and under the influences of a meal. The present invention has been completed based on this finding.

DISCLOSURE OF THE INVENTION

The present invention relates to a sustained-release metal valproate tablet which comprises a core tablet comprising a metal valproate having on the surface a coating layer comprising light silicic acid anhydride dispersed in a mixture of ethyl cellulose and a methacrylic acid-methyl methacrylate copolymer (hereinafter referred to as a "methacrylic acid copolymer").

Furthermore, the present invention relates to a sustained-release metal valproate tablet having two coating layers which comprises the above-described sustained-release metal valproate tablet having further on the surface a coating layer comprising light silicic acid anhydride dispersed in ethyl cellulose.

The present invention will be described in greater detail. Cores of the metal valproate tablets which can be used in the present invention are not particularly limited, and any tablets prepared by conventional techniques can be used as they are. Such tablets are prepared by, for example, adding an additive, such as a vehicle, a binders, or the like, mixing them, granulating the mixture in a conventional manner, adding an appropriate lubricant thereto, and punching the mixture. These additives are used for improvement of molding properties, regulation of granule size, and protection against moisture.

The vehicles used in the preparation of the cores include crystalline cellulose, calcium sulfate, light silicic acid anhydride, and higher fatty acid metal salts. The binders include water-soluble polymers, for example, hydroxypropyl cellulose, hydroxypropylmethyl cellulose, polyvinylpyrrolidone, polyethylene glycol, and the like; water-insoluble polymers, for example, ethyl cellulose, polyvinyl chloride, aminoalkyl methacrylate copolymer RS (specified in Japanese Pharmaceutical Excipients), and the like; and enteric polymers, for example, hydroxypropylmethyl cellulose phthalate, methacrylic acid copolymer L, cellulose acetate phthalate, hydroxypropylmethyl cellulose acetate succinate, carboxyvinyl polymer, and the like. The lubricants include calcium stearate, magnesium stearate, hydrated silicon dioxide, light silicic acid anhydride, and the like.

The metal composing the metal valproate used in the cores includes alkali metals, alkaline earth metals, and the like. Na is preferred as the alkali metal, and Ca is preferred as the alkaline earth metal. Sodium valproate is especially preferred as the metal valproate in the present invention.

The process for preparing the sustained-release metal valproate tablets according to the present invention is not particularly limited. The tablets are generally prepared by coating cores containing a metal valproate with a mixed solution (coating agent) which comprises ethyl cellulose and a methacrylic acid copolymer and has light silicic acid anhydride uniformly dispersed therein by spray coating in a usual manner. The resulting sustained-release tablets can further be coated with a solution of ethyl cellulose having light silicic acid anhydride dispersed therein by spray coating in a usual manner to provide sustained-release tablets with a double coating layer.

A preferred embodiment of the preparation of the sustained-release tablets according to the present invention is given below.

Light silicic acid anhydride which is dispersed in a mixed solution of ethyl cellulose and a methacrylic acid copolymer is selected from those which are insoluble in water or organic solvents and dispersible in water or organic solvents to form colloidal suspensions. Such light silicic acid anhydrides are described in The Pharmacopoeia of Japan XII and are commercially available under the trade name of, for example, Aerosil-200 (produced by Nippon Aerosil Co., Ltd.). The light silicic acid anhydride has preferably a particle size of 7 to 16 μm.

While ethyl cellulose used in the present invention is not particularly limited so long as it is capable of forming a film, an ethyl ether of cellulose having an ethoxy group content of 46 to 51% is usually employed. This ethyl cellulose is described in Japanese Pharmaceutical Excipients and commercially available under the trade name, for example, of Ethocel Standard (produced by Dow Chemical Co., Ltd.) and the like.

Furthermore, the methacrylic acid copolymer includes copolymers having a methacrylic acid:methyl methacrylate molar ratio of 1:1 to 1:2, such as methacrylic acid copolymer L described in Japanese Pharmaceutical Excipients (Eudragit L; methacrylic acid:methyl methacrylate=1:1 (by mole)) and methacrylic acid copolymer S (Eudragit S, produced by Rohm Pharma; methacrylic acid:methyl methacrylate=1:2 (by mole)). Methacrylic acid copolymer L is preferably used.

Plasticizers customarily used in coating agents can be used in the invention to provide sufficient stability and flexibility to the coating layer. Examples of the plasticizers include polyethylene glycol, glycerol fatty acid esters, triethyl citrate, and the like.

The methacrylic acid copolymer can be used in an amount of 0.1 to 1 part by weight, preferably 0.1 to 0.5 part by weight, per part by weight of ethyl cellulose. Ethyl cellulose and the methacrylic acid copolymer are used in the form of a mixed solution in an appropriate solvent, such as methanol, ethanol, isopropyl alcohol, and the like.

In the present invention, the coating agent is prepared by dissolving ethyl cellulose and a methacrylic acid copolymer in ethanol, or the like, usually in a total concentration of 2 to 10% by weight, preferably 4 to 7% by weight, and dispersing in the mixed solution usually 0.05 to 0.5 part by weight, preferably 0.1 to 0.3 part by weight, of light silicic acid anhydride per part by weight of the mixture of ethyl cellulose and methacrylic acid copolymer. The coating agent is usually applied to the core to a coating weight of 1 to 20% by weight, preferably about 2.5 to 8% by weight, based on the weight of the core.

The rate of dissolution of the metal valproate from the sustained-release tablets thus obtained can be controlled by varying the mixing ratio of the methacrylic acid copolymer to ethyl cellulose, the mixing ratio of the light silicic acid anhydride to the mixture of ethyl cellulose and methacrylic acid copolymer, or the amount of the coating agent applied.

More specifically, if the methacrylic acid copolymer is 0.1 to 1 part by weight, preferably 0.1 to 0.5 part by weight, per part by weight of ethyl cellulose, preferred sustained-release tablets that are hardly affected by pH conditions are obtained (see Test Example 2). The higher the ratio of light silicic acid anhydride to the mixture of ethyl cellulose and methacrylic acid copolymer or the lower the coating weight, the faster the overall dissolution. Conversely, the lower the light silicic acid anhydride ratio or the higher the coating weight, the slower the overall dissolution (see Test Example 3). If the coating agent does not at all contain light silicic acid anhydride, the initial dissolution is inhibited by a high coating weight so that the time lag in dissolution becomes noticeable, or sufficient sustained release properties cannot be obtained at a low coating weight, failing to furnish preferred sustained-release tablets (see Test Examples 4 and 6).

Moreover, in the present invention, if desired, the thus prepared sustained-release tablet can further have a conventional sustained-release coat or a sugar coat.

It is also possible to form the sustained-release coating layer according to the present invention on the surface of a sustained-release metal valproate tablet having a slightly higher dissolution rate that is prepared by conventional techniques.

For example, sustained-release metal valproate tablets having a double coating layer can be prepared by spray coating the sustained-release tablets obtained as described above with a lower alcohol solution of ethyl cellulose having dispersed therein 0.1 to 0.7 part by weight of light silicic acid anhydride per part by weight of ethyl cellulose in accordance with the process of JP-A-6-40899.

The thus prepared sustained-release metal valproate tablets having a double coating layer can have its total coating weight reduced below the coating weight of a single coating layer and yet can be freed of the influences of a meal and a pH.

BEST MODE FOR CARRYING OUT THE INVENTION

EXAMPLES

Figure 1:
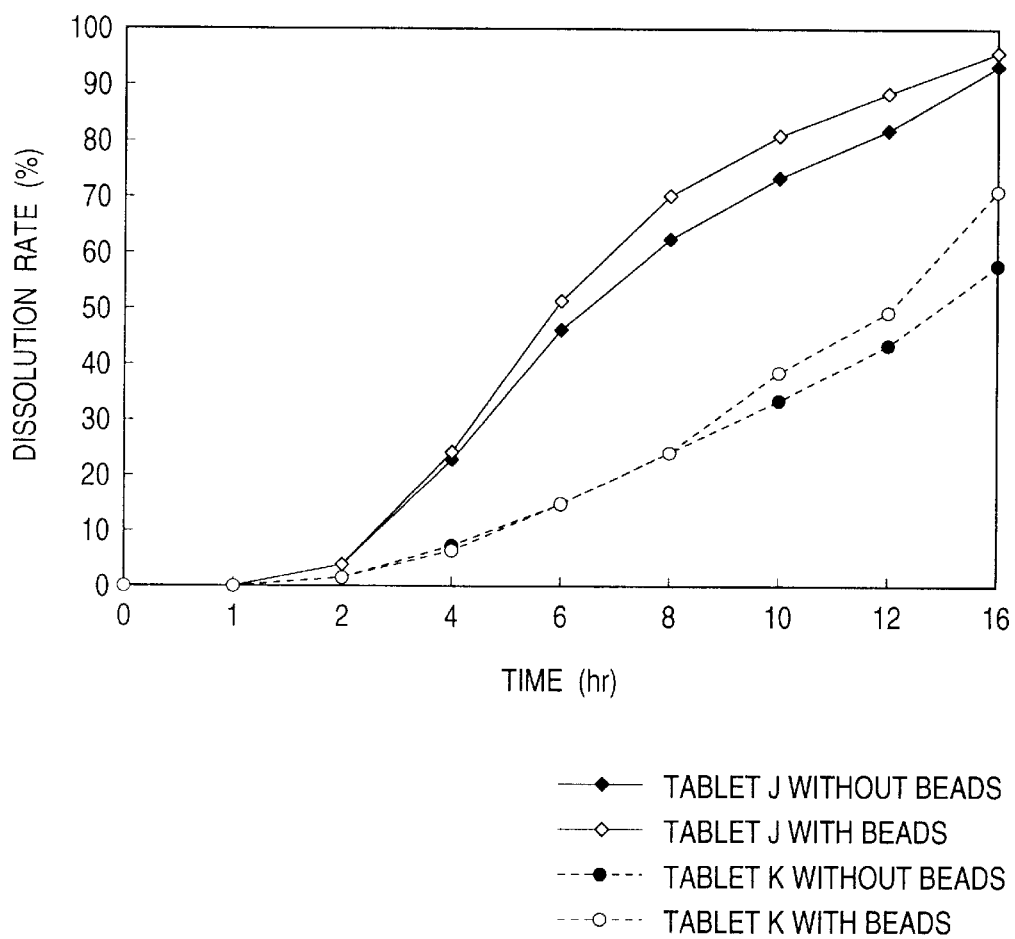
FIG. 1 is a graph of dissolution rate with time with or without the influences of a meal.

The present invention will now be illustrated in greater detail with reference to Examples, Comparative Examples, and Test Examples.

Unless otherwise indicated, the light silicic acid anhydride used was "Aerosil-200" produced by Nippon Aerosil Co., Ltd.; ethyl cellulose having an ethoxy content of 46 to 51% was used; and the fluidized bed coating apparatus used was "Uniglat" manufactured by Okawara Seisakusho Co., Ltd.

Example 1

(A) Preparation of Cores

Sodium valproate weighing 3000 g and 300 g of light silicic acid anhydride were mixed thoroughly, and 990 g of a 5 wt % ethanol solution of hydroxypropyl cellulose and 100 g of ethanol were added thereto, followed by kneading. The blend was dried in a hot air drier at 70° C. and passed through a 16-mesh sieve. The resulting granules were mixed with 0.7 wt % calcium stearate and compression molded with a couplet punch (diameter 13×6.5 mm) to obtain tablets (weight 450 mg).

(B) Preparation of Sustained-Release Tablets

A thousand core tablets obtained in (A) above were fluidized in a fluidized bed coating apparatus and spray-coated with a coating agent comprising an ethanol solution containing 4 wt % ethyl cellulose and 2 wt % methacrylic acid copolymer L (Eudragit L) and having dispersed therein 1.5 wt % light silicic acid anhydride to obtain sustained-release sodium valproate tablets (Tablet A: weight 490 mg)).

Example 2

(A) Preparation of Cores

Sodium valproate weighing 3000 g, 150 g of light silicic acid anhydride, and 300 g of ethyl cellulose were mixed thoroughly, and 900 g of ethanol was added thereto, followed by kneading. The blend was dried in a hot air drier at 70° C. and passed through a 16-mesh sieve. The resulting granules were mixed with 0.7 wt % calcium stearate and compression molded with a couplet punch to obtain tablets (weight 460 mg).

(B) Preparation of Sustained-Release Tablets

A thousand core tablets obtained in (A) above were fluidized in a fluidized bed coating apparatus and spray-coated with a coating agent comprising an ethanol solution containing 4 wt % ethyl cellulose and 2 wt % methacrylic acid copolymer L and having dispersed therein 1.5 wt % or 3 wt % light silicic acid anhydride to obtain sustained-release sodium valproate tablets B-1, B-2, B-3, C-1, C-2, and C-3. The proportion (wt %) of the light silicic acid anhydride in the coating agent, the amount of the coating agent used, and the weight of the coating layer of the resulting coated tablets are shown in Table 1 below.

TABLE 1

| | Tablet | | | | | |
|---|---|---|---|---|---|---|
| | B-1 | B-2 | B-3 | C-1 | C-2 | C-3 |
| Light silicic acid anhydride (%) | 1.5 | 1.5 | 1.5 | 3 | 3 | 3 |
| Amount of Coating Agent (g) | 1000 | 1500 | 2000 | 1000 | 1500 | 2000 |
| Weight of Coating Layer (mg) | 26.9 | 42.9 | 56.3 | 32.3 | 47.7 | 65.9 |

Example 3

(A) Preparation of Cores

Sodium valproate weighing 600 g and 30 g of calcium stearate, and 60 g of ethyl cellulose were mixed thoroughly, and 130 g of ethanol was added thereto, followed by kneading. The blend was dried in a hot air drier at 70° C. and passed through a 16-mesh sieve. The resulting granules were mixed with 0.5 wt % calcium stearate and compression molded with a couplet punch to obtain tablets (weight 462 mg).

(B) Preparation of Sustained-Release Tablets

A thousand core tablets obtained in (A) above were fluidized in a fluidized bed coating apparatus and spray-coated with a coating agent comprising an ethanol solution containing 4 wt % ethyl cellulose and 2 wt % methacrylic acid copolymer L and having dispersed therein 1.5 wt % light silicic acid anhydride to obtain sustained-release sodium valproate tablets (Tablet D: weight 500 mg).

Example 4

(A) Preparation of Cores

Sodium valproate weighing 600 g and 60 g of light silicic acid anhydride were mixed thoroughly, and 198 g of a 5 wt % ethanol solution of hydroxypropyl cellulose and 20 g of ethanol were added thereto, followed by kneading. The blend was dried in a hot air drier at 70° C. and passed through a 16-mesh sieve. The resulting granules were mixed with 0.7 wt % calcium stearate and compression molded with a round punch (diameter 11 mm) to obtain tablets (weight 452 mg).

(B) Preparation of Sustained-Release Tablets

A thousand core tablets obtained in (A) above were fluidized in a fluidized bed coating apparatus and spray-coated with a coating agent comprising an ethanol solution containing 4 wt % ethyl cellulose and 2 wt % methacrylic acid copolymer L and having dispersed therein 1.5 wt % light silicic acid anhydride to obtain sustained-release sodium valproate tablets (Tablet E: weight 491 mg).

Example 5

A thousand core tablets obtained in Example 2 (weight 460 mg) were fluidized in a fluidized bed coating apparatus and spray-coated with a coating agent comprising an ethanol solution containing 4 wt % ethyl cellulose, 2 wt % methacrylic acid copolymer L, and 1.5 wt % triethyl citrate (Citroflex 2 (SC-60), produced by Pfizer, Inc.) and having dispersed therein 1.5 wt % light silicic acid anhydride to obtain sustained-release sodium valproate tablets (Tablet F: weight 528 mg).

Example 6

A thousand core tablets prepared in Example 2 (weight 460 mg) were fluidized in a fluidized bed coating apparatus and spray-coated with a coating agent comprising an ethanol solution containing 4 wt % ethyl cellulose, 2 wt % methacrylic acid copolymer L, and 1.5 wt % triethyl citrate and having dispersed therein 0.9 wt % light silicic acid anhydride to obtain sustained-release sodium valproate tablets (Tablet G: weight 492 mg).

Examples 7 to 11

A thousand core tablets prepared in Example 2 were fluidized in a fluidized bed coating apparatus and spray-coated with a coating agent comprising an ethanol solution having the composition shown in Table 2 below to obtain coating sodium valproate tablets. The coating solution used in each case further contained triethyl citrate as a plasticizer and light silicic acid anhydride each in an amount of 25% based on the ethyl cellulose/methacrylic acid copolymer L (Eudagit L) mixture.

TABLE 2

| Example | Ethyl Cellulose (%) | Eudragit L (%) | Ratio |
|---------|---------------------|----------------|-------|
| 7       | 4                   | 0.4            | 1:0.1 |
| 8       | 4                   | 1              | 1:0.25|
| 9       | 4                   | 2              | 1:0.5 |
| 10      | 3                   | 3              | 1:1   |
| 11      | 2                   | 4              | 1:2   |

Example 12

A thousand core tablets prepared in the same manner as in Example 2(a) (weight 460.4 mg, diameter 13×6.5 mm) were fluidized in a fluidized bed coating apparatus and spray-coated with a coating agent comprising an ethanol solution containing 4 wt % ethyl cellulose, 2 wt % methacrylic acid copolymer L, and 1.5 wt % triethyl citrate and having dispersed therein 1.5 wt % light silicic acid anhydride to obtain sustained-release sodium valproate tablets (Tablet H: weight 496.2 mg).

Example 13

(Primary Coating

Two hundred thousand cores prepared in the same manner as in Example 2(A) (weight 462 mg, diameter 13×6.5 mm) were rotated on a pan coating apparatus and spray-coated with a coating agent comprising an ethanol solution containing 4 wt % ethyl cellulose, 2 wt % methacrylic acid copolymer L and 1.5 wt % triethyl citrate and having dispersed therein 1.5 wt % light silicic acid anhydride to obtain primarily coated tablets (weight 477 mg).
(B) Secondary Coating Two hundred thousand primarily coated tablets obtained in (A) above were rotated on a pan coating apparatus and spray-coated with a coating agent comprising a 4 wt % ethyl cellulose solution in ethanol having dispersed therein 2 wt % light silicic acid anhydride to obtain double-coated sustained-release sodium valproate tablets (Tablet J: weight 483 mg, and Tablet K: weight 487 mg).

Comparative Examples 1 to 6

A thousand core tablets obtained in Example 1 (Comparative Examples 1 to 5) or Example 2 (Comparative Example 6) were coated with a coating agent having the following composition in the same manner as in Example 1 to prepare coated tablets of sodium valproate.

Comparative Example 1

A 4 wt % ethanol solution of ethyl cellulose.

Comparative Example 2

A 4 wt % ethanol solution of ethyl cellulose having dispersed therein 1.5 wt % light silicic acid anhydride.

Comparative Example 3

A solution of 4 wt % ethyl cellulose and 2 wt % hydroxypropylmethyl cellulose in ethanol.

Comparative Example 4

A solution of 4 wt % ethyl cellulose and 2 wt % hydroxypropylmethyl cellulose phthalate in a mixture of ethanol and water.

Comparative Example 5

A solution of 4 wt % ethyl cellulose and 4 wt % metaaminoalkyl methacrylate copolymer RS in ethanol.

Comparative Example 6

A solution of 4 wt % ethyl cellulose and 2 wt % methacrylic acid copolymer L in ethanol.

Test Example 1 (Dissolution Test of Coating Film)

The tablets obtained in Example 1 and Comparative Examples 1 to 6 were cut cross-sectionally, and the core was removed to separate the coating film. The coating film (about 0.25 cm$^2$) was put in valproic acid, and any change of the film was observed. The results were as follows.
Coating Film of Example 1:
  The coating film showed no change even after 24 hours.
Coating Film of Comparative Example 1:
  The coating film dissolved completely in 1 to 2 hours.
Coating Film of Comparative Example 2:
  The coating film dissolved completely in 1 to 2 hours.
Coating Film of Comparative Example 3:
  The coating film dissolved completely in 2 to 3 hours.
Coating Film of Comparative Example 4:
  The coating film dissolved completely in 5 to 6 hours.
Coating Film of Comparative Example 5:
  The coating film dissolved completely in 5 to 6 hours.
Coating Film of Comparative Example 6:
  The coating film showed no change even after 24 hours.
  It can be seen from the above results that the coating films composed of ethyl cellulose and the methacrylic acid copolymer do not at all dissolve in valproic acid.

Test Example 2 (Dissolution Test)

The tablets obtained in Examples 7 to 11 were tested according to the second method of dissolution test (paddle method) specified in The Pharmacopoeia of Japan XII. The number of rotation was 100 rpm. Nine hundred milliliters each of the first solution (pH: 1.2) and the second solution (pH: 6.8) used in a disintegration test method specified in The Pharmacopoeia of Japan were used as a testing solution. The system under the test was sampled at a certain time interval, and the amount of sodium valproate dissolved out was measured by HPLC.

The results of the dissolution test (dissolution rate; %) are shown in Table 3 below. It can be seen from Tables 2 and 3 that a preferred ethyl cellulose:methacrylic acid copolymer L ratio is in the range of 1:0.1 to 1:1, particularly 1:0.1 to 1:0.5, in which range the difference in dissolution between the first and second solutions (The Pharmacopoeia of Japan) is small.

TABLE 3

Dissolution Test (Dissolution Rate: %)

| Ex. | Testing Soln. | Time of Dissolution (hr) | | | | | 1st/2nd Soln. Difference | |
|-----|---------------|---|---|---|---|---|---|---|
|     |               | 2 | 4 | 6 | 8 | 12 | 4 hrs | 6 hrs |
| 7   | 1st Soln.     | 16.7 | 38.4 | 53.9 | 64.5 | 80.3 | 21.7 | 25.9 |
|     | 2nd Soln.     | 23.6 | 60.1 | 79.8 | 89.7 | 97.0 |      |      |
| 8   | 1st Soln.     | 7.4  | 34.6 | 53.9 | 63.9 | 75.2 | 20.0 | 22.2 |
|     | 2nd Soln.     | 11.0 | 54.6 | 76.1 | 87.9 | 96.1 |      |      |
| 9   | 1st Soln.     | 9.1  | 37.7 | 62.3 | 71.8 | 80.6 | 20.8 | 17.9 |
|     | 2nd Soln.     | 18.1 | 58.5 | 80.2 | 97.8 | 98.4 |      |      |

TABLE 3-continued

Dissolution Test (Dissolution Rate: %)

| Ex. | Test-ing Soln. | Time of Dissolution (hr) 2 | 4 | 6 | 8 | 12 | 1st/2nd Soln. Difference 4 hrs | 6 hrs |
|---|---|---|---|---|---|---|---|---|
| 10 | 1st Soln. | 17.5 | 43.4 | 61.2 | 73.0 | 82.6 | 42.7 | 36.1 |
|    | 2nd Soln. | 52.9 | 86.1 | 97.3 | 98.9 | 100.7 | | |
| 11 | 1st Soln. | 12.5 | 30.5 | 57.3 | 75.4 | 83.9 | 60.0 | 43.4 |
|    | 2nd Soln. | 60.9 | 90.5 | 100.7 | 102.5 | 103.1 | | |

Note:

1st Soln.: The first solution (pH: 1.2) used in the disintegration test specified in The Pharmacopoeia of Japan.

2and Soln.: The second solution (pH: 6.8) used in the disintegration test specified in The Pharmacopoeia of Japan.

Test Example 3 (Dissolution Test)

Tablets B-1 to B-3 and C-1 to C-3 obtained in Example 2 (tablets having a varied coating weight) were tested in accordance with the second method of dissolution test (paddle method) specified in The Pharmacopoeia of Japan XII. The number of rotation was 100 rpm. Distilled water was used as a testing solution. The system under the test was sampled at a certain time interval, and the amount of sodium valproate dissolved out was measured by HPLC.

The results of the dissolution test (dissolution rate; %) are shown in Table 4 below. It can be seen from Table 4 that the dissolution is faster as the coating weight, namely, the thickness of the coating layer decreases and as the light silicic acid anhydride ratio in the coating layer increases.

TABLE 4

Dissolution Test of Tablets with Varied Coating Weight (Dissolution Rate; %)

| Tablet | Testing Soln. | Time of Dissolution (hr) 2 | 4 | 8 | 12 |
|---|---|---|---|---|---|
| B-1 | distilled water | 53.5 | 84.3 | 102.2 | 103.2 |
| B-2 | distilled water | 21.3 | 62.6 | 98.0 | 103.2 |
| B-3 | distilled water | 4.7 | 35.7 | 84.8 | 98.3 |
| C-1 | distilled water | 66.9 | 91.3 | 98.6 | 99.9 |
| C-2 | distilled water | 55.5 | 85.3 | 97.5 | 98.3 |
| C-3 | distilled water | 37.7 | 76.0 | 97.8 | 100.3 |

Test Example 4 (Dissolution Test)

Tablets A to G obtained in Examples 1 to 6 and the tablets obtained in Comparative Example 6 were tested in accordance with the second method of dissolution test (paddle method) specified in The Pharmacopoeia of Japan XII. The number of rotation was 100 rpm. Nine hundred milliliters each of the first solution (pH 1.2) and the second solution (pH 6.8) specified in a disintegration method of The Pharmacopoeia of Japan were used as a testing solution. The system under the test was sampled at a certain time interval, and the amount of sodium valproate dissolved out was measured by HPLC.

The results of the dissolution test are shown in Table 5 below. As is seen from Table 5, the sustained-release tablets of the present invention exhibit sustained release properties in a stable manner, being little influenced by the pH of the testing solution. To the contrary the tablets coated with a coating agent containing no light silicic acid anhydride show a considerable time lag, hardly dissolving in the initial stage.

TABLE 5

Dissolution Test (Dissolution Rate; %)

| Tablet | Testing Soln. | Time of Dissolution (hr) 2 | 4 | 8 | 12 |
|---|---|---|---|---|---|
| A | 1st soln. | 28.1 | 60.5 | 82.3 | 89.0 |
|   | 2nd soln. | 29.0 | 72.3 | 99.4 | 101.2 |
| B-3 | 1st soln. | 2.7 | 17.1 | 60.9 | 71.9 |
|     | 2nd soln. | 6.2 | 37.4 | 83.8 | 97.2 |
| C-3 | 1st soln. | 12.2 | 37.0 | 68.3 | 77.2 |
|     | 2nd soln. | 37.0 | 72.9 | 96.9 | 99.6 |
| D | 1st soln. | 18.0 | 51.8 | 73.6 | 85.5 |
|   | 2nd soln. | 29.6 | 68.1 | 93.7 | 99.5 |
| E | 1st soln. | 12.2 | 42.7 | 87.5 | 94.0 |
|   | 2nd soln. | 33.8 | 70.3 | 97.2 | 100.4 |
| F | 1st soln. | 8.7 | 37.0 | 70.9 | 80.0 |
|   | 2nd soln. | 18.1 | 58.6 | 91.7 | 98.6 |
| G | 1st soln. | 28.3 | 56.8 | 85.8 | 97.6 |
|   | 2nd soln. | 31.9 | 66.1 | 91.7 | 95.1 |
| Comp. Ex. 6 | 1st soln. | 0.0 | 7.9 | 57.3 | 70.5 |
|             | 2nd soln. | 0.1 | 3.4 | 42.6 | 74.0 |

Test Example 5 (Dissolution Test in Consideration for the Influence of a Meal)

The dissolution behavior of Tablet G obtained in Example 6 and the tablets obtained in Comparative Example 2 in a dissolution test in consideration for the influences of a meal into consideration was compared with that in the second method of a dissolution test (paddle method) specified in The Pharmacopoeia of Japan. In the dissolution test with consideration for the influences of a meal (test with beads), a test tablet, a testing solution (900 ml of the first solution (pH 1.2) of a disintegration test specified in The Pharmacopoeia of Japan) and about 1400 plastic beads (each measuring 6 mm in diameter and weighing about 115 mg, totaling 160 g) were put in a beaker of a dissolution tester, and the mixture was rotated with a paddle at 25 rpm. The mixture was sampled at a certain time interval, and the amount of sodium valproate dissolved out was measured by HPLC. The dissolution test with no influences of a meal (test without beads) was carried out using the same testing solution as described above in the same manner as in Test Example 4.

The test results of Tablet G and the tablets of Comparative Example 2 are shown in Tables 6 and 7, respectively. These results prove that the sustained-release tablets of the present invention (Tablet G) exhibit sustained release properties in both the dissolution test with consideration for the influences of a meal and The Pharmacopoeia of Japan dissolution test second method (paddle method), whereas the sustained-release tablets prepared by a conventional technique (the tablets of Comparative Example 2) do not show sufficient sustained release properties in the test with consideration for the influences of a meal because the coating layer suffers from destruction by the beads.

TABLE 6

Dissolution Test on Tablet G

| Time (hr) | With Beads Dissolution Rate (%) | S.D. | Without Beads Dissolution Rate (%) | S.D. |
|---|---|---|---|---|
| 1 | 4.2 | 0.6 | 2.4 | 4.6 |
| 2 | 34.9 | 3.6 | 28.3 | 4.3 |
| 4 | 61.5 | 6.7 | 56.8 | 3.8 |
| 6 | 73.5 | 6.4 | 73.0 | 3.3 |
| 8 | 80.6 | 7.4 | 85.8 | 2.7 |
| 12 | 87.1 | 3.8 | 97.6 | 0.9 |

TABLE 7

Dissolution Test on Tablets of Comparative Example 2

| Time (hr) | With Beads Dissolution Rate (%) | S.D. | Without Beads Dissolution Rate (%) | S.D. |
|---|---|---|---|---|
| 1 | 6.1 | 0.5 | 5.7 | 0.4 |
| 2 | 17.9 | 5.1 | 14.3 | 1.2 |
| 3 | 59.9 | 27.9 | 24.7 | 1.7 |
| 4 | 85.8 | 20.4 | 34.9 | 1.6 |
| 6 | — | — | 51.9 | 2.0 |
| 8 | — | — | 66.0 | 6.9 |
| 12 | — | — | 83.5 | 3.1 |

Test Example 6 (Dissolution Test under Various Conditions)

Tablets J and K obtained in Example 13(B) were subjected to the same dissolution test as in Test Example 4 and the same dissolution test with consideration for the influences of a meal as conducted in Test Example 5.

The test results are shown in Table 8 below and FIG. 1. From these results it can be seen that the double-coated tablets, prepared by providing a secondary coating layer comprising ethyl cellulose and light silicic acid anhydride on the tablets having a primary coating layer which are hardly influenced by a meal (single-coated tablets), control the dissolution of sodium valproate effectively. To increase the amount of a coating agent to be sprayed might be a conceivable means for controlling the dissolution rate. In this case, however, the tablet generally tends to have an increased delay (time lag) in starting dissolving. Hardly was observed such extension of time lag with the double-coated tablets.

Where a double coating layer was provided, it was possible to control the dissolution rate of sodium valproate with a smaller amount of the coating agent as compared with the single-coated tablets. Further, the resulting double-coated tablets were satisfactorily free from the influences of a meal and a pH condition similarly to the single-coated tablets.

TABLE 8

Dissolution Test on Tablets of Example 13 (Dissolution Rate; %)

| Tablet | Testing Soln. | Beads | Time of Dissolution (hr) | | | | | | | |
|---|---|---|---|---|---|---|---|---|---|---|
| | | | 1 | 2 | 4 | 6 | 8 | 10 | 12 | 16 |
| J | 1st Soln. | absent | 0.2 | 2.1 | 12.2 | 45.1 | 65.2 | 72.3 | 78.3 | 88.6 |
| | | present | 3.2 | 5.4 | 15.6 | 31.8 | 56.2 | 73.7 | 86.7 | 93.9 |
| | 2nd Soln. | absent | 0.4 | 4.2 | 22.9 | 45.7 | 62.4 | 73.6 | 82.0 | 93.5 |
| | | present | 0.0 | 4.3 | 24.4 | 50.9 | 70.1 | 80.9 | 88.5 | 95.8 |
| K | 1st Soln. | absent | 0.0 | 1.8 | 6.1 | 10.5 | 19.7 | 29.3 | 38.9 | 53.8 |
| | | present | 0.0 | 0.0 | 4.0 | 10.9 | 16.4 | 25.1 | 32.0 | 57.2 |
| | 2nd Soln. | absent | 0.2 | 1.8 | 7.6 | 14.8 | 24.1 | 34.3 | 44.4 | 59.1 |
| | | present | 0.0 | 1.5 | 6.5 | 14.9 | 24.6 | 39.1 | 50.1 | 72.1 |

Test Example 7 (Oral Administration Test in Rabbit)

Tablets B-3 and C-3 of Example 2, Tablet F of Example 5, and the tablets of Comparative Example 6 were given orally to healthy male rabbits (Japanese white rabbit) with 20 ml water at a dose of one tablet/body. After 2, 4, 6, 8 and 24 hours from the administration, 1 ml of blood was taken from the auricular vein. The serum was separated from the blood sample, and the concentration of valproic acid in the serum was determined by gas chromatography.

The results obtained are shown in Table 9 below. It is seen from Table 9 that the sustained-release tablets of the present invention maintain a satisfactory blood concentration in animals for an extended period of time, whereas the tablet of Comparative Example 6 hardly dissolves in the initial stage, showing a large time lag, and abruptly increases its dissolution rate after passage of a certain time.

TABLE 9

Blood Concentration of Valproic Acid in Rabbit (μg/ml)

| Tablet | Time After Administration (hr) | | | | |
|---|---|---|---|---|---|
| | 2 | 4 | 6 | 8 | 24 |
| B-3 | 9.5 | 21.6 | 45.8 | 49.4 | 19.8 |
| C-3 | 33.8 | 44.5 | 69.2 | 25.1 | 11.2 |
| G | 25.4 | 43.9 | 41.2 | 42.3 | 5.5 |
| Comp. Example 6 | 0.2 | 6.4 | 87.9 | 113.5 | 6.2 |

Test Example 8 (Pharmacokinetic Test in Human)

A single dose of one tablet/body of the sustained-release sodium valproate Tablet H prepared in Example 12 was administered to each of 6 healthy male adults having been fasted. Blood samples (2 ml each) were taken before administration and after 1, 2, 4, 6, 8, 10, 12, 24, 36, 48, and 60 hours from administration, and the blood concentration was determined by HPLC.

After at least 1 week from the final collection of blood samples, the same 6 subjects who had been ingested were given the same tablet at a dose of one tablet/body, and the blood concentration of the drug was measured in the same manner. The results are shown in Tables 10 and 11 and FIG. 2.

TABLE 10

Human Blood Concentration (μg/ml) of Valproic Acid on Administration at Fasting or at Ingestion

| Subject | | Time After Administration (hr) | | | | | | | | | | |
|---|---|---|---|---|---|---|---|---|---|---|---|---|
| | | 1 | 2 | 4 | 6 | 8 | 10 | 12 | 24 | 36 | 48 | 60 |
| Fasting | Avg. | 5.0 | 13.1 | 22.8 | 26.5 | 24.7 | 22.7 | 19.3 | 10.2 | 6.3 | 3.7 | 2.4 |
| | S.D. | 4.2 | 7.0 | 4.4 | 3.3 | 3.5 | 4.0 | 4.6 | 3.9 | 2.9 | 2.2 | 1.6 |
| Inges- | Avg. | 2.2 | 9.5 | 25.2 | 28.2 | 25.2 | 23.3 | 19.8 | 10.9 | 6.4 | 3.9 | 2.5 |
| tion | S.D. | 1.7 | 5.0 | 8.0 | 6.7 | 5.9 | 4.5 | 4.7 | 3.7 | 2.9 | 2.0 | 1.5 |

TABLE 11

Comparison on Pharmacokinetic Parameter

| Parameter | At Fasting | At Ingestion |
|---|---|---|
| AUCO-60 (μg/ml.hr) | 610.6 ± 173.8 [100.0] | 627.9 ± 188.6 [102.8] |
| Cmax (μg/ml) | 26.7 ± 3.4 [100.0] | 29.3 ± 8.0 [109.7] |
| Tmax (hr) | 6.0 ± 1.3 | 5.3 ± 1.0 | mean ± S.D., n = 6

Note: The values in the brackets mean relative values taking the results of the administration at fasting as 100%.

Figure 2:
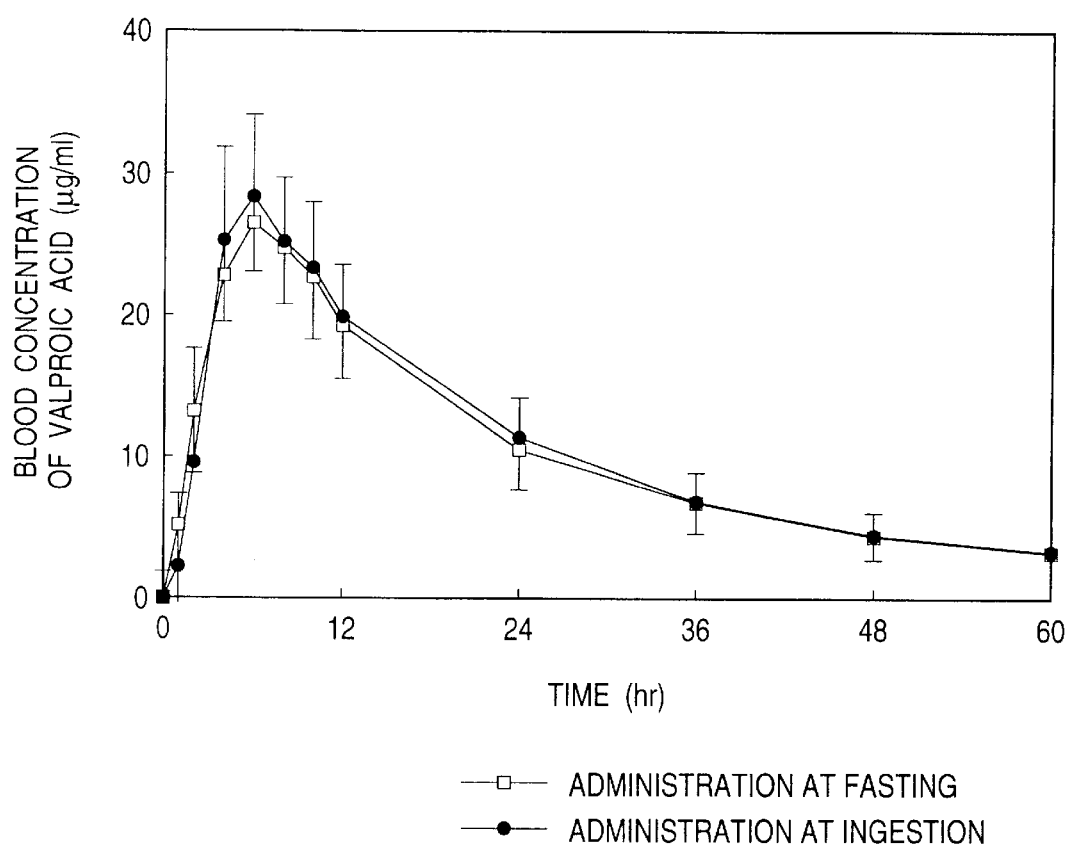
FIG. 2 is a graph showing changes of valproic acid concentration in human blood with time.

The results of Tables 10 and 11 and FIG. 2 prove that the sustained-release tablets according to the present invention maintain a stable concentration of valproic acid in blood for a prolonged period of time irrespective of whether the subject has been fasted or ingested.

Industrial Applicability

The sustained-release tablets according to the present invention maintain a stable dissolution rate for an extended period of time in a dissolution test using testing solutions having different pH values and a dissolution test designed with consideration for the influences of a meal. When administered to humans, the tablets maintain a stable blood concentration in an extended period of time. Therefore, the tablets are excellent in sustained release of a metal valproate.

What is claimed is:

1. A sustained-release metal valproate tablet which comprises a core tablet comprising a metal valproate having on the surface a coating layer comprising light silicic acid anhydride dispersed in a mixture of ethyl cellulose and a methacrylic acid-methyl methacrylate copolymer.

2. The sustained-release metal valproate tablet according to claim 1, wherein the metal valproate is sodium valproate.

3. The sustained-release metal valproate tablet according to claim 1, wherein the methacrylic acid-methyl methacrylate copolymer is present in the coating layer in an amount of 0.1 to 1 part by weight per part by weight of ethyl cellulose.

4. The sustained-release metal valproate tablet according to claim 1, wherein the light silicic acid anhydride is present in the coating layer in an amount of 0.05 to 0.5 part by weight per part by weight of the mixture of ethyl cellulose and the methacrylic acid-methyl methacrylate copolymer.

5. The sustained-release metal valproate tablet according to claim 1, wherein the methacrylic acid-methyl methacrylate copolymer has a methacrylic acid to methyl methacrylate ratio of 1:1 by mole.

6. The sustained-release metal valproate tablet according to claim 1, wherein the coating layer further comprises a plasticizer.

7. The sustained-release metal valproate tablet according to any one of claims 1 to 6, wherein the weight of the coating layer is 1 to 20% by weight based on the weight of the core tablet.

8. A sustained-release metal valproate tablet having two coating layers which comprises the sustained-release metal valproate tablet according to any one of claims 1 to 6 having on the surface a coating layer comprising light silicic acid anhydride dispersed in ethyl cellulose.

9. A sustained-release metal valproate tablet having two coating layers which comprises the sustained-release metal valproate tablet according to claim 7 having on the surface a coating layer comprising light silicic acid anhydride dispersed in ethyl cellulose.

* * * * *